United States Patent [19]
Watson et al.

[11] Patent Number: 5,176,675
[45] Date of Patent: Jan. 5, 1993

[54] USE OF LASERS TO BREAK DOWN OBJECTS FOR REMOVAL FROM WITHIN THE BODY

[75] Inventors: Graham M. Watson, London, England; Horace W. Furumoto, Wellesley, Mass.

[73] Assignee: The General Hospital Corporation, Boston, Mass.

[21] Appl. No.: 625,639

[22] Filed: Dec. 7, 1990

Related U.S. Application Data

[63] Continuation of Ser. No. 726,472, Apr. 24, 1985, abandoned.

[51] Int. Cl.⁵ ............................................. A61B 17/32
[52] U.S. Cl. ................................... 606/15; 606/3; 606/128
[58] Field of Search ..................... 128/395–398; 606/3, 13–16, 128

[56] References Cited

U.S. PATENT DOCUMENTS

| | | | |
|---|---|---|---|
| 3,890,578 | 6/1975 | Wang | 372/102 |
| 4,092,530 | 5/1978 | Wise | 372/31 |
| 4,146,019 | 5/1979 | Bass et al. | 128/6 |
| 4,207,874 | 6/1980 | Choy | 128/6 |
| 4,273,127 | 6/1981 | Auth et al. | 128/303.1 |
| 4,309,998 | 1/1982 | Rosa et al. | |
| 4,418,688 | 0/1983 | Loeb | |
| 4,470,414 | 9/1984 | Imagawa et al. | 128/303.1 |
| 4,478,217 | 10/1984 | Shimeeki et al. | 128/303.1 |
| 4,498,183 | 2/1985 | Leuatter | 372/87 |
| 4,503,854 | 3/1985 | Jako | 128/303.1 |
| 4,520,816 | 1/1985 | Schacher et al. | 128/303.1 |
| 4,538,613 | 9/1985 | Rosenberg | 128/395 |
| 4,549,091 | 10/1985 | Fahlen et al. | 372/38 |

FOREIGN PATENT DOCUMENTS

| | | |
|---|---|---|
| 0153847 | 4/1985 | European Pat. Off. |
| 0144764 | 6/1985 | European Pat. Off. |
| 0152766 | 8/1985 | European Pat. Off. |
| 2412690 | 10/1974 | Fed. Rep. of Germany |
| 2538960 | 4/1977 | Fed. Rep. of Germany |
| 8500510 | 2/1985 | PCT Int'l Appl. |
| 8503631 | 8/1985 | PCT Int'l Appl. |

OTHER PUBLICATIONS

Watson, 2nd British Conference on Lasars in Medicine and Surgury, Dec. 13, 1983.
Burlamacchi et al., "A Simple, Reliable Waveguide Dye Laser for Ophthalmological Applications," *Rev. Sci. Instrum.*, 46:3 (Mar. 1975).
Paul et al, "The Effect of Temperature and Other Factors on Selective Microvascular Damage Caused by Pulsed Dye Laser," *The Journal of Investigative Dermatology*, 81:333–336 (1983).
Parrish et al., "Selective Thermal Effects with Pulsed Irradiation from Lasers: From Organ to Organelle," *Journal of Investigative Dermatology*, 80:075s–080s (1983).
Greenwald, et al., "Comparative Histological Studies of the Tunable Dye (at 577 nm) Laser and Argon Laser: The Specific Vascular Effects of the Dye Laser," *Journal of Investigative Dermatology* 77:305–310 (1981).
Watson, "Laser Fragmentation of Urinary Calculi," *Lasers in Urologic Surgery* (Chicago: Year Book Medical Publishers, Inc., 1985) 120–137.
Anderson et al, "Selective Photothermolysis: Precise Microsurgery by Selective Absorption of Pulsed Radiation," *Science*, 220:524–527, (Apr. 23, 1983).
Beckman, et al., "Limbectomies, Keratectomies, and Kera-Tosotomies Performed with a Rapid-Pulsed Carbon Dioxide Laser", *American Journal of Ophthalmology*, 71:1277–1283 (1971).

(List continued on next page.)

*Primary Examiner*—Max Hindenburg
*Attorney, Agent, or Firm*—Fish & Richardson

[57] ABSTRACT

Calculi, stones, or calcified tissue are broken down for removal from within a body using laser pulses that are delivered via an optical fiber and have a wavelength and pulse duration selected to break down the object into smaller particles without delivering energy sufficient to cause damage to other tissue.

16 Claims, 3 Drawing Sheets

OTHER PUBLICATIONS

Abela, et al., "Effects of Carbon Dioxide, Nd-YAG, and Argon Laser Radiation on Coronary Atheromatous Plaques," *The American Journal of Cardiology*, 50:1199–1205 (1982).

*Lasers in Surgery and Medicine*, 5:2 (1985), abstracts cited on pp. 000911–000916.

Anderholm, "Laser-Generated Stress Waves," *Applied Physics Letter*, vol. 16, No. 3, Feb. 1, 1970, 113–115.

Yang, "Stress Waves Generated in Thin Metallic Films by a Q-Sqitched Ruby Laser," *Journal of Applied Physics*, vol. 45, No. 6, Jun. 1974, 2601–2608.

Orii et al., *Surgery*, 90:120–122 (Jul. 1981).

Schmidt-Kloiber et al., *Biomedizinische Technik* 30:173 (Aug. 1985).

Linsker et al., "Far-UV laser ablation of atherosclerotic lesions" (Apr. 1984) *Lasers Surg. Med.*, 4, 201–206.

Gerrity et al., "Arterial response to laser operation for removal of atherosclerotic plaques," (Mar. 1983) *J. Thoracic Cardio. Surg.*, 85, 409–421.

Choy et al., "Laser coronary angioplasty: Experience with 9 cadaver hearts," (Dec. 1982) *Am. J. Cardiol.*, 50, 1029–1211.

Sanborn et al., "In vivo argon laser radiation of rabbit atherosclerotic lesions" Abstract from Texas Heart Institute Meetings, Oct. 13–15, 1983.

Watson et al., "Laser fragmentation of renal calculi," (Jan. 1983) *Brit. J. Urol.*, 55, 613–616.

Orii et al., "Lithotomy of intrahepatic and choledochal stones with YAG laser," (Apr. 1983), Surg. Gynecol. & obst., 156, 485–488.

Watson et al., "Laser fragmentation of renal calculi," (Jan. 1983) *Lasers Surg. Med.*, 3, 115.

Fair, "In vitro destruction of urinary calculi by laser induced stress waves," (Mar. 1978) Med. Instrument., 12, 100–105.

Tanahashi et al., "Disintegration of urinary calculi by laser beam: Drilling experiment . . . " (Mar. 1979) *Tohoku J. exp Med*, 128, 189–196.

Tanahashi et al., "Transurethral disintegration of urinary calculi by the use of laser beam," *Urology*, Jan. 1982.

Mulvaney et al., "The laser beam in urology" (Jan. 1968) *J. Urology*, 112–115.

Watson et al., "Tunable pulsed dye laser for fragmentation of biliary calculi," Abstract for Am. Soc. Laser Med. and Surg. (1985).

Schmidt-Kloiber, "Energy Transformer for Stone Destruction in the Evacuating Urinary Passages of Human Beings," *Nephrology Today*, Journal 1, 1978, 117–146.

Reichel and Schmidt-Kloiber, "The Application of Laser-Induced Waves to the Example of the Destruction of Urinary Calculi," *Medizinische Physik* Oct. 1983, 197–201.

Schmidt-Kloiber et al., "Laserinduced Shock-Wave Lithotripsy (LISL)," *Biomed. Technik*, 30 (Aug. 1985), 173–181.

Wang, "Dye Lasers and their Application in Ophthalmology," *New Frontiers in Laser Medicine and Surgery*, Sep. 1983, 215–222.

Tanahashi and Orikasa, "The Use of Laser Beam in Urology," (Jan. 1979).

USE OF LASERS TO BREAK DOWN OBJECTS FOR REMOVAL FROM WITHIN THE BODY

This is a continuation of U.S. Ser. No. 06/726,472 filed Apr. 24, 1985 now abandoned.

BACKGROUND OF THE INVENTION

This invention relates to using a laser beam delivered via an optical fiber to break down a calculus, stone, or calcified tissue for removal from within the body.

Frequently such calculi, stones, or calcified tissue are located in positions which can be reached using only small diameter endoscopes and the optical fiber must be fine enough to pass via the endoscope. The stones are typically in close proximity to healthy tissue.

SUMMARY OF THE INVENTION

The general feature of the invention is in delivering via the optical fiber laser pulses having a wavelength and pulse duration which will break down the calculus, stone, or calcified tissue into smaller particles without delivering energy sufficient to cause damage to other tissue in the same vicinity.

The preferred embodiments include the following features. The pulses are at wavelengths corresponding to wavelengths for which the object has a relatively shallow depth of penetration, preferably wavelengths between 350 and 550 nanometers (most preferably 351, 504, or 450 nanometers). The laser is either of the pulsed dye or excimer type. The pulses have durations of at least 10 nanoseconds (preferably between 0.5 and 2 microseconds, and the pulse energy is no greater than 0.200 joules, preferably between 0.025 and 0.150 joules. The fiber is flexible and has a core diameter no greater than 1000 microns, preferably between 200 and 600 microns. The distal end of the fiber is in contact with the object (a stone) and the interface between them is surrounded by fluid The laser pulses are applied in brief bursts, and remaining fragments are broken down by one-shot pulses.

The stone is safely and relatively quickly broken down into easily removed sand-like particles, without melting. Thermal damage to surrounding tissue is limited. The stone and the particles are not propelled into the surrounding tissue. Degradation of the optical fiber by the laser beam is limited. The fiber can be sufficiently small in diameter to be useful with small diameter endoscopes.

Other advantages and features of the invention will become apparent from the following description of the preferred embodiment, and from the claims.

DESCRIPTION OF THE PREFERRED EMBODIMENT

We first briefly describe the drawings.

DRAWINGS

STRUCTURE

Figure 1:
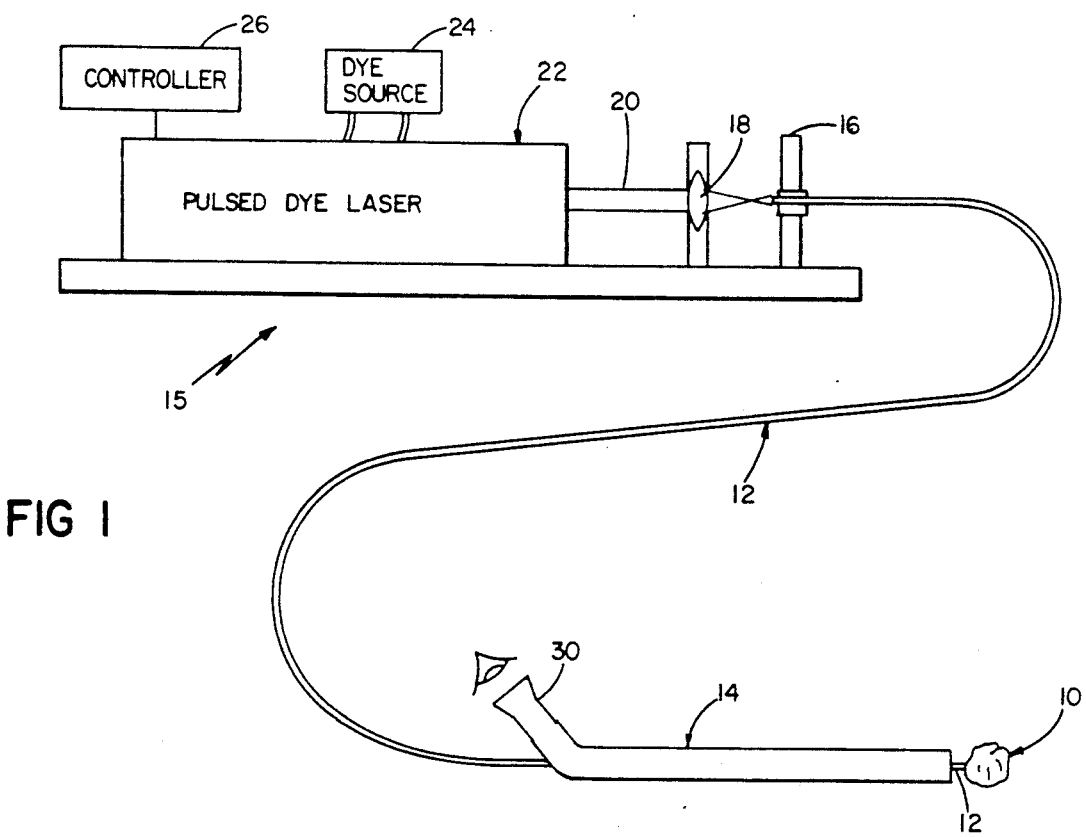
FIG. 1 is a diagram of a system for breaking down unwanted objects or tissue.

Referring to FIG. 1, a urinary calculus (stone) 10 to be removed from within a human body is contacted by the cleaved distal face of a flexible quartz silica optical fiber 12 (Superquide series available from Fibreguide Industries) having a core diameter in the range of 200 to 1000 microns. Fiber 12 passes through a ureteroscope 14 and extends to a laser source 15, where the proximal face of fiber 12 is held in a fiber mount 16 (Model FP2 available from Newport Corporation). The proximal face of fiber 12 is exposed to receive, via a convergent lens 18 (of appropriate focal length for the fiber), a beam 20 from a linear flash lamp pumped pulsed dye laser 22. Laser 22 is connected to a source 24 of dye of a selected wavelength characteristic. Laser 22 is also connected to a controller 26 which includes a control panel to permit the user to activate and deactivate the laser and to vary the pulse energy and pulse repetition rate of the laser beam. Laser 22 and controller 26 are available from Candela Corporation, Natick, Mass.

Ureteroscope 14 includes an eyepiece 30 through which the user can observe the stone and the distal end of the fiber, as well as a light source (not shown) to illuminate the distal end for viewing and an irrigation lumen to deliver a irrigant to the distal end.

The wavelength at which the laser will be operated (and hence the dye to be used) is chosen in part on the basis of the percentage transmission characteristics of the stone material. For example, the percentage transmission of calcium phosphate and calcium oxalate stone materials for different wavelengths was measured experimentally (by conventional spectroscopy) on sections of dry stones which were sanded to form progressively thinner wafers. The resulting graph of the log of the percentage transmission against thickness was linear indicating the following 1/e depths of penetration for different wavelengths.

| | 1/e Depth of Penetration (mm) | |
|---|---|---|
| Wavelength (nm) | Calcium Phosphate | Calcium Oxalate |
| 1064 | 2.16 ± 0.8 | 3.58 ± 0.85 |
| 577 | 0.81 ± 0.2 | 0.50 ± 0.1 |
| 504 | 0.54 ± 0.05 | 0.30 ± 0.2 |
| 450 | 0.42 ± 0.05 | 0.24 ± 0.05 |
| 308 | 0.25 ± 0.03 | 0.18 ± 0.1 |

The penetration depth decreases with shorter wavelengths. The smallest penetration depth is the most desirable from the point of view of enabling a low energy threshold to accomplish fragmentation, producing small size fragments, and limiting the propulsion of fragments into surrounding tissue. Very short wavelengths (shorter than 350 nm) in the ultraviolet range (for example 308 nm), however, are known to be mutagenic and are difficult to deliver via the optical fiber and therefore ar avoided. Wavelengths in the range 450 to 550 nanometers are preferred. Dyes are available which operate at the 450 nm (blue) and 504 nm (green) wavelengths. The 450 nm dye fades fairly rapidly. Where the cost of the dye is an issue, the best choice is the 504 nm dye.

Figure 2:
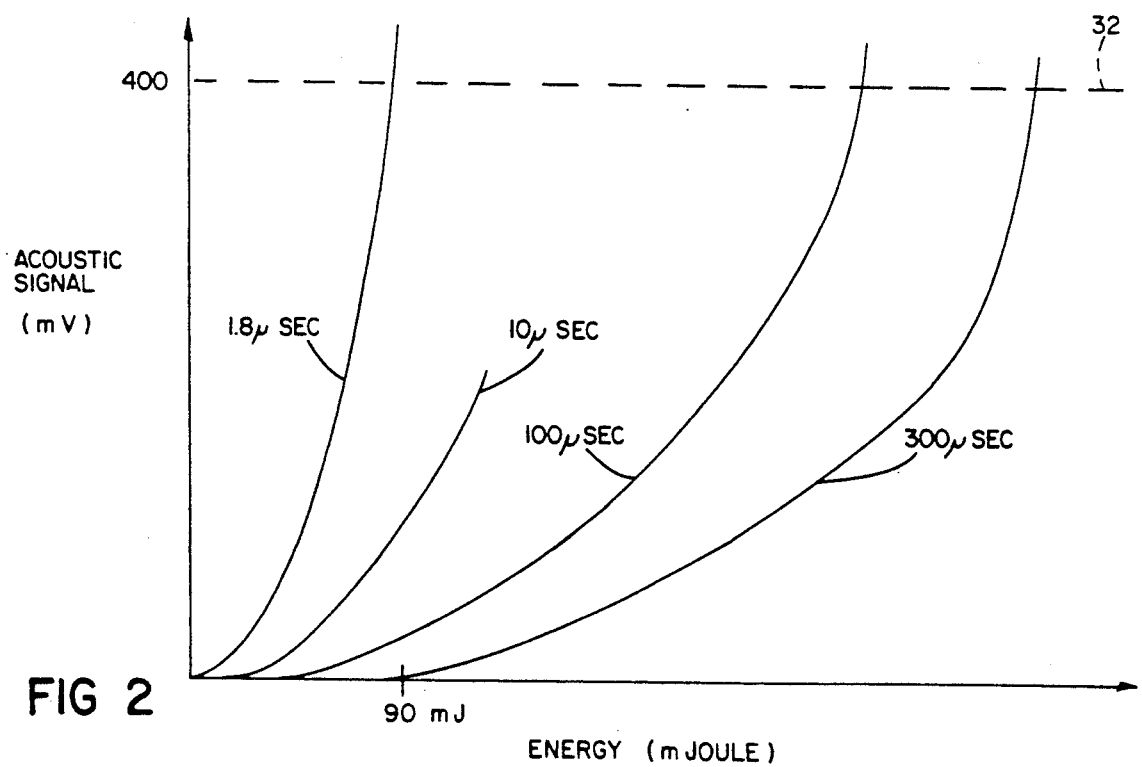
FIG. 2 is a family of curves showing fragmentation thresholds versus pulse energy for different pulse durations.

The duration of each pulse delivered by the laser is chosen to minimize the energy delivered to the stone while still accomplishing fragmentation (i.e., the breaking down of the stone into smaller particles). Referring to FIG. 2, the threshold energy in milliJoules per pulse required to initiate fragmentation of an oxalate stone for a given pulse duration at 577 nm using a 600 micron optical fiber was determined experimentally by measuring an acoustic signal in the stone resulting from the pulse. The acoustic signal was measured electronically in millivolt units. Dashed line 32 represents the acoustic level (nominally 400 millivolts) which corresponds to the initiation of fragmentation in a stone. Each curve represents, for a given pulse duration, the variation of acoustic signal with energy per pulse. The point at which each curve crosses line 32 is the threshold pulse energy level at which fragmentation will occur. The threshold energy level decreases with decreasing pulse duration. Because lower energy pulses are less likely to cause thermal damage or to propel the stone or the broken off particles into surrounding tissue, pulse durations of less than 10 microseconds, preferably between 0.5 and 2.0 microseconds, are used.

Figure 3:
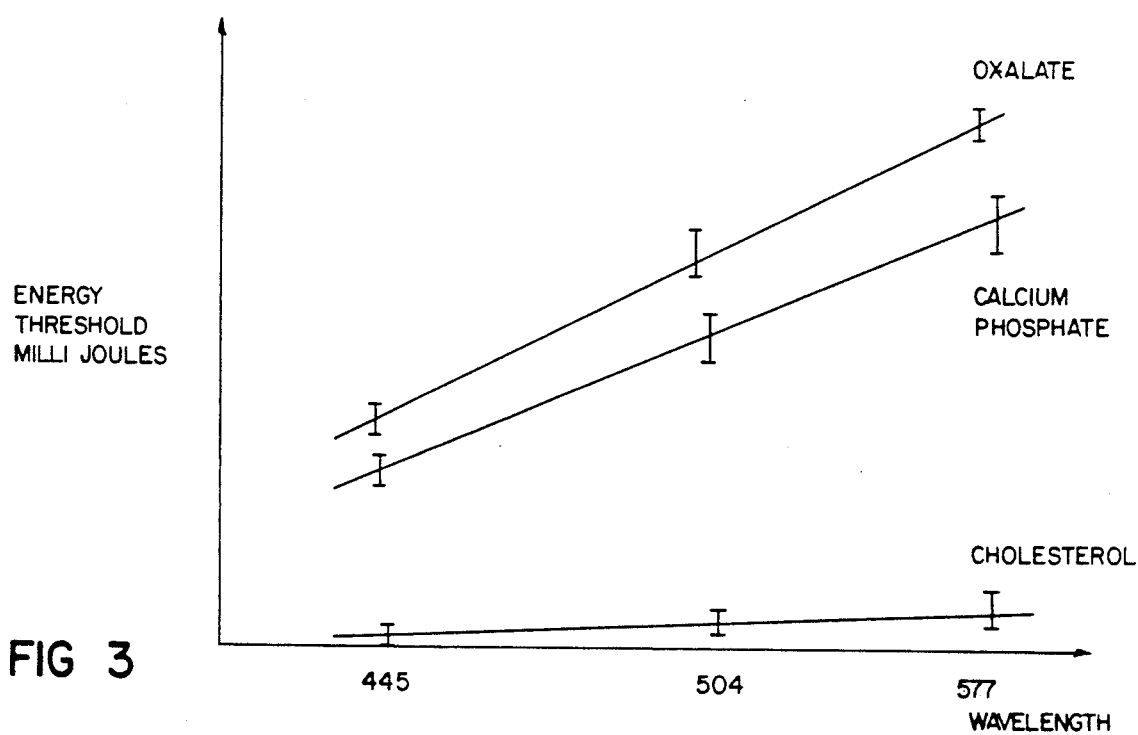
FIG. 3 is a family of curves indicative of fragmentation threshold pulse energy versus wavelength for different types of stones.

Referring to FIG. 3, the pulse energy threshold for causing an acoustic signal at a given level (25 millivolts) was determined for three different stone types at three different wavelengths, further confirming the desirability of using shorter wavelengths regardless of the stone material.

Figure 4:
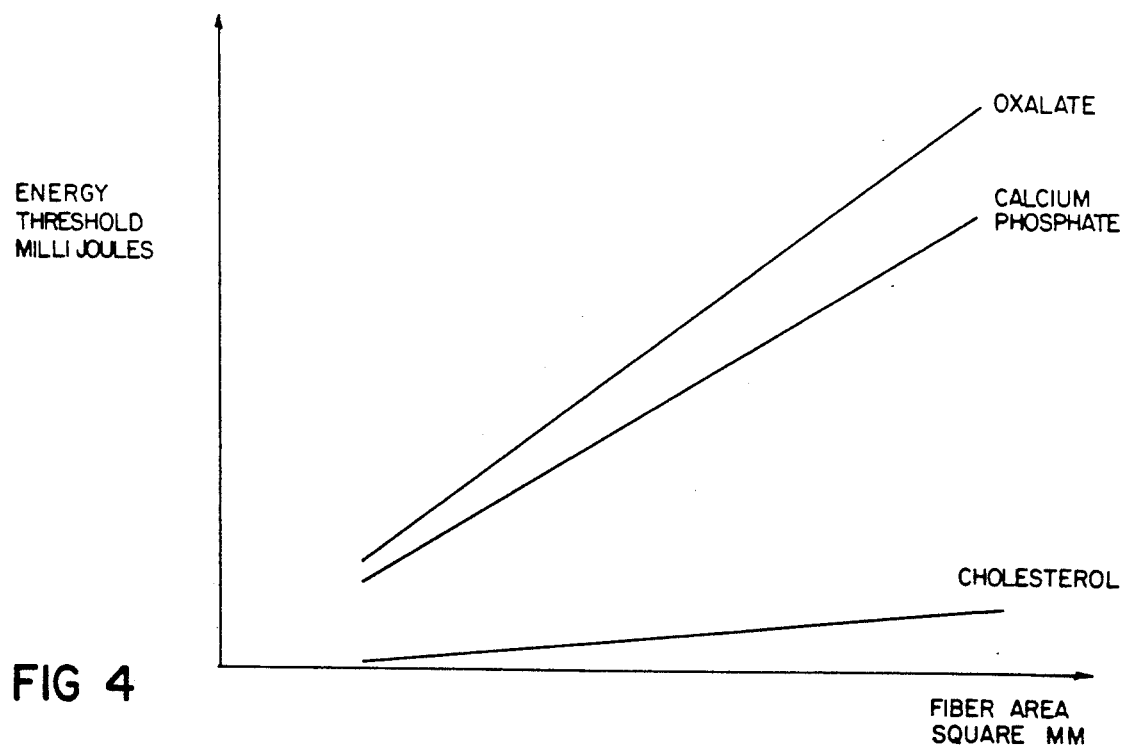
FIG. 4 is a family of curves indicative of fragmentation threshold pulse energy versus fiber area for different types of stones.

Referring to FIG. 4, the relationship between cross-sectional area of fiber 12 and the threshold pulse energy required to cause an acoustic signal at the 25 mv level was determined for three different stone materials. In all cases the threshold pulse energy decreases linearly with fiber area. Three different fiber sizes were used: 1000, 600, and 400 microns.

Figure 5:
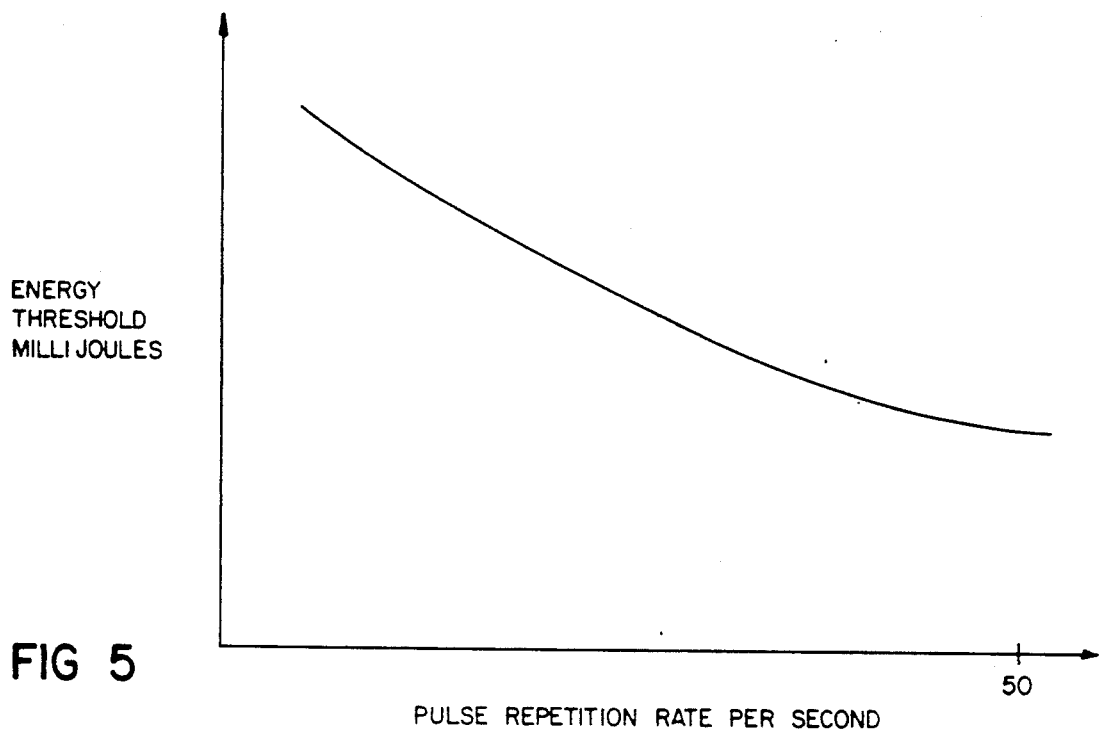
FIG. 5 is a curve indicative of fragmentation threshold pulse energy versus pulse repetition rate.

The pulse repetition rate may also be chosen to reduce the threshold pulse energy at which fragmentation is expected to occur. Referring to FIG. 5, the energy required to produce the 25 mv acoustic signal decreased with increasing pulse repetition rate. Furthermore, at higher repetition rates, the fragmentation proceeds more rapidly. At higher repetition rates, however, the dye is depleted faster and the optical fiber is less capable of passing the energy to the stone. A maximum practical rate is about 50 Hertz.

It can be shown experimentally that above the energy pulse threshold, the average weight of fragments yielded per pulse increased sharply and that laminated oxalate stones have a substantially lower fragmentation threshold than do homogeneous oxalate stones. Thus the pulse energy can be varied to break down different stones.

OPERATION

In operation, after inserting the ureteroscope 14 to reach the site at which the stone 10 is located, the distal end of the fiber 12 is inserted through the ureteroscope and oriented by sight, so that the distal face of the fiber is in contact with the stone 10. The site is irrigated via a lumen in the ureteroscope. The laser is set at a wavelength between 450 and 550 nanometer by selecting an appropriate dye. The pulsed dye laser controller 22 is adjusted to set the pulse energy, and pulse repetition rate. The laser pulse energy is initially set at a value which is lower than the threshold fragmentation level and then increased until the desired fragmentation effect has been attained. Preferably the pulsed dye laser is operated at about 30 millijoules per pulse for a 200 micron fiber and about 100–150 millijoules per pulse for a 600 micron fiber, and in no event more than about 200 millijoules. The pulse repetition rate is set between 10 and 50 Hertz.

Figure 6:
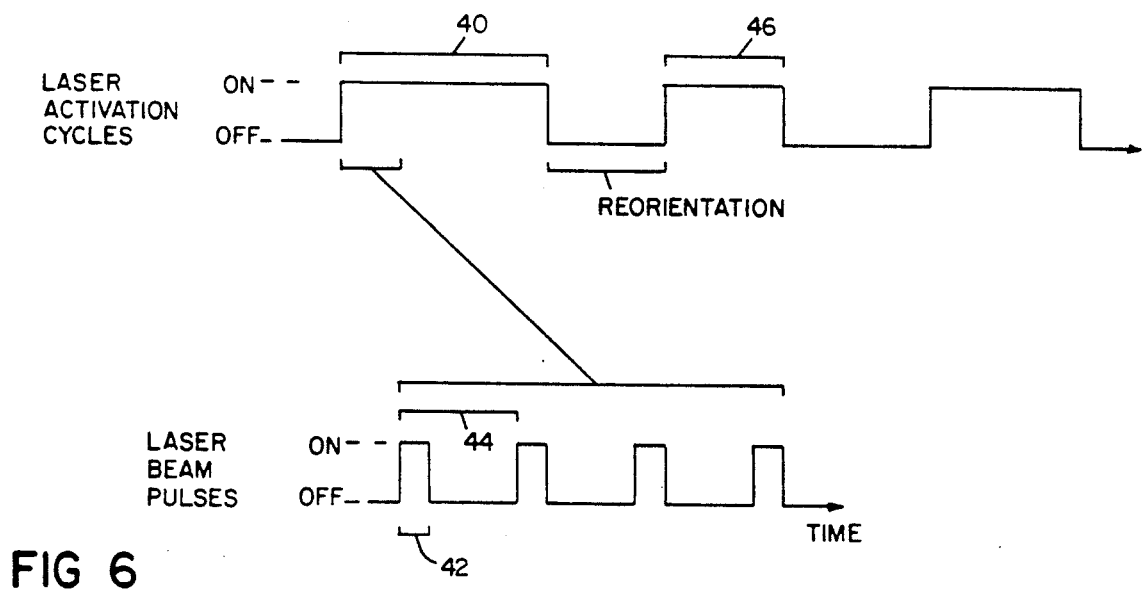
FIG. 6 is a diagram of pulse timing.

Referring to FIG. 6, the laser 22 is activated for a brief burst, for example for a period of a second or a fraction of a second (identified as 40 in FIG. 6). The laser pulse duration 42 is typically between 0.5 and 2.0 microseconds. The period of the pulse repetition is identified as 44 on FIG. 6. During activation period 40, a portion of the stone breaks down into a combination of vapor and sand-like particles small enough to be easily removed.

The distal face of the fiber is then reoriented (during a period identified as such in FIG. 6) to be once again in contact with the stone. Then the laser is again activated briefly for a burst period 46, to cause another portion of the stone to break down. The process is repeated until the entire stone has been broken down. Any fragments which need to be broken down further can then be broken down by touching them with the distal end of the fiber and applying a single shot laser pulse.

The stone is safely and relatively quickly broken down into easily removed sand like particles, without melting. Thermal damage to surrounding tissue is limited. The stone and the particles are not propelled into the surrounding tissue. Degradation of the optical fiber by the laser beam is limited. The fiber can be sufficiently small in diameter to be useful with small diameter endoscopes.

Other embodiments are within the following claims.

For example, laser 22 can be an excimer laser tuned to a particular wavelength by a selected gas mixture. The wavelength is chosen to be as short as possible while still permitting the pulses to be delivered via the optical fiber. Preferably the gas mixture is xenon fluoride providing a wavelength of 351 nm. The resulting pulses have very shallow penetration into the stone and operate to break the stone into extremely fine particles and vapor. Progress through the stone is slower per pulse than for the pulsed dye laser, but this is offset by higher pulse repetition rates which are possible with the excimer laser. The pulse durations typical of excimer lasers are 10 nanoseconds but can be lengthened by various techniques to 80 or more nanoseconds. Such pulse durations make the pulses somewhat more difficult to deliver via the optical fiber than the pulsed dye laser pulses.

Using the excimer laser on an oxalate calculus via a 1000 micron fiber at 351 nm, a repetition rate of 200 Hertz, and a pulse energy of 30 millijoules (energy density of 1.6 joules/cm$^2$), produced an average yield of fragments per pulse of 10 micrograms. By comparison, using the pulsed dye laser at 450 nm and a pulse energy of 20 joules/cm$^2$ via a 600 micron fiber generated 100 micrograms of fragments per pulse. Using the pulsed dye laser at 504 nm at a pulse energy of 25 joules/cm, via a 600 micron fiber yielded 100 micrograms of fragments per pulse, and at 30 joules/cm$^2$ yielded 1 milligram per pulse.

The product of breaking down the stone is about 90% vapor for the excimer laser and 10% for the pulsed dye laser.

In other embodiments, gallstones or calcified arterial plaque may be broken down by a pulsed dye laser at 450 nm, and any appropriate technique for reaching the stone with the distal end of the fiber may be used.

We claim:

1. Apparatus for breaking down a calculus, stone, or calcified tissue for removal from within a body, comprising a source of laser pulses, a wavelength regulator arranged to regulate the wavelength of said pulses, an optical fiber having a proximal end arranged to receive said pulses from said source and a distal end arranged to deliver said pulses to the surface of said object, and a pulse controller connected to said laser pulse source and arranged to control the duration of said pulses, said pulses having a duration of less than 10.0 microseconds and to maintain the energy delivered in each said pulse at a level no greater than 0.2 joules, said source of pulses, said wavelength regulator, and said pulse controller being further arranged to cause said pulses to have a wavelength and a pulse duration such that said pulses break down said calculus, stone, or calcified tissue into smaller particles without delivering energy sufficient to cause damage to other tissue in the vicinity of said calculus, stone, or calcified tissue.

2. The apparatus of claim 1 wherein said wavelength is between 350 and 550 nanometers.

3. The apparatus of claim 1 wherein said laser pulse source comprises a tunable dye laser and said wavelength regulator comprises a dye material.

4. The apparatus of claim 1 wherein said laser pulse source comprises an excimer laser and said wavelength regulator comprises a gas mixture.

5. The apparatus of claim 1 wherein said wavelength is 504 nanometers.

6. The apparatus of claim 1 wherein said wavelength is 450 nanometers.

7. The apparatus of claim 1 wherein said wavelength is 351 nanometers.

8. The apparatus of claim 1 wherein said pulses have a duration of at least 10 nanoseconds.

9. The apparatus of claim 1 wherein said pulses have a duration of between 0.5 microseconds and 2 microseconds.

10. The apparatus of claim 1 wherein said source and said pulse controller are arranged to maintain the energy delivered in said pulse at a level between 25 and 150 millijoules.

11. The apparatus of claim 1 wherein said optical fiber has a core diameter no greater than 1000 microns, preferably between 200 and 600 microns.

12. The apparatus of claim 1 further comprising an endoscope capable of permitting the user to view the site at which said pulses are delivered.

13. The apparatus of claim 1 wherein the interface between said distal end and said calculus, stone or calcified tissue is surrounded by fluid.

14. The apparatus of claim 1 wherein said fiber is flexible.

15. The apparatus of claim 1 wherein said distal end is in contact with said calculus, stone, or calcified tissue.

16. Apparatus for breaking down a calculus, stone, or calcified tissue for removal from within a body, comprising a pulsed laser operating at a wavelength of between 350 and 550 nanometers, an optical fiber having a distal end in contact with said calculus, stone, or calcified tissue, and a proximal end which receives laser pulses from said laser, said pulses having durations of between 10 nanoseconds and 10.0 microseconds.

* * * * *

UNITED STATES PATENT AND TRADEMARK OFFICE
CERTIFICATE OF CORRECTION

PATENT NO. : 5,176,675
DATED : January 5, 1993
INVENTOR(S) : Graham M. Watson , et al It is certified that error appears in the above-indentified patent and that said Letters Patent is hereby corrected as shown below:

On the title page: UNDER "OTHER PUBLICATIONS", line 1, correct the spelling of "Lasers", and line 2, correct the spelling of "Surgery";

page 2, column 1, "Choy et al.", under "OTHER PUBLICATIONS", correct "1029-1211" to --1209-1211--;

Column 2, line 65, correct the spelling of "are";

Column 4, line 60, please correct "25 joules/cm$_2$" to --25 joules/cm$^2$--;

Column 6, claim 16, line 28, change "within a body", to --within the body--.

Signed and Sealed this

Fourth Day of January, 1994

Attest:

BRUCE LEHMAN

Attesting Officer    Commissioner of Patents and Trademarks